(12) United States Patent
Baram et al.

(10) Patent No.: US 11,690,551 B2
(45) Date of Patent: Jul. 4, 2023

(54) LEFT ATRIUM SHAPE RECONSTRUCTION FROM SPARSE LOCATION MEASUREMENTS USING NEURAL NETWORKS

(71) Applicant: Biosense Webster (Israel) Ltd., Yokneam (IL)

(72) Inventors: Alon Baram, Yokneam Ilit (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1036 days.

(21) Appl. No.: 16/459,760

(22) Filed: Jul. 2, 2019

(65) Prior Publication Data

US 2020/0029845 A1    Jan. 30, 2020

Related U.S. Application Data

(60) Provisional application No. 62/711,814, filed on Jul. 30, 2018.

(51) Int. Cl.
*G06N 3/08*    (2023.01)
*A61B 5/0538*    (2021.01)
(Continued)

(52) U.S. Cl.
CPC .............. *A61B 5/287* (2021.01); *A61B 5/316* (2021.01); *G06N 3/04* (2013.01); *G06N 3/08* (2013.01); *A61B 5/0538* (2013.01); *A61B 5/6852* (2013.01); *A61B 5/7207* (2013.01); *A61B 2576/023* (2013.01); *G06T 17/00* (2013.01); *G06T 2207/20084* (2013.01)

(58) Field of Classification Search
CPC . G06T 2207/20084; G06T 2207/10072; G06T 2207/20076; G06T 2207/20081; G06T 2207/30048; G06T 7/55; G06T 2200/08; G06T 7/149; G06T 17/00; G06T 2210/41; G06V 20/653; A61B 5/287; A61B 5/316; A61B 5/0538; A61B 5/6852; A61B 5/7207; A61B 2576/023; G06N 3/04; G06N 3/08; G06N 3/0454
See application file for complete search history.

(56) References Cited

U.S. PATENT DOCUMENTS 6,760,468 B1    7/2004    Yeh et al.
8,456,182 B2    6/2013    Bar-Tal et al.
(Continued)

OTHER PUBLICATIONS

Cretu et al. "Neural Network Architecture for 3D Object Representation." Proceedings, 2nd IEEE International Workshop on Haptic, Audio and Visual Environments and Their Applications, Sep. 21, 2003, pp. 31-36 (Year: 2003).*
(Continued)

*Primary Examiner* — Jon Chang
(74) *Attorney, Agent, or Firm* — Scully, Scott, Murphy & Presser, PC

(57) ABSTRACT

A method includes, in a processor, receiving example representations of geometrical shapes of a given type of organ. In a training phase, a neural network model is trained using the example representations. In a modeling phase, the trained neural network model is applied to a set of location measurements acquired in an organ of the given type, to produce a three-dimensional model of the organ.

18 Claims, 3 Drawing Sheets

(51) Int. Cl.
*G06T 17/00* (2006.01)
*A61B 5/287* (2021.01)
*G06N 3/04* (2023.01)
*A61B 5/316* (2021.01)
*A61B 5/00* (2006.01)

(56) References Cited

U.S. PATENT DOCUMENTS

| | | |
|---|---|---|
| 9,576,107 B2 | 2/2017 | Safran et al. |
| 2004/0252870 A1 | 12/2004 | Reeves et al. |
| 2012/0071751 A1* | 3/2012 | Sra .................. A61B 6/541 600/424 |
| 2014/0152653 A1 | 6/2014 | Dala-Krishna |
| 2014/0254900 A1 | 9/2014 | Sturm |
| 2015/0178938 A1 | 6/2015 | Gorman et al. |
| 2017/0046616 A1 | 2/2017 | Socher et al. |
| 2019/0053728 A1* | 2/2019 | Yang .................. A61B 5/0044 |
| 2019/0261945 A1 | 8/2019 | Funka-Lea et al. |

OTHER PUBLICATIONS

Maury et al. "Three-Dimensional Mapping in the Electrophysiological Laboratory." Archives of Cardiovascular Disease (2018) 111, Jun. 7, 2018, pp. 456-464 (Year: 2018).*
Zhong, Hua et al: ""Virtual Touch": An Efficient Registration Method for Catheter Navigation in Left Atrium", Oct. 1, 2006 (Oct. 1, 2006), Advances in Biometrics : International Conference, ICB 2007, Seoul, Korea, Aug. 27-29, 2007; Proceedings; [Lecture Notes in Computer Science; Lect.Notes Computer], Springer, Berlin, Heidelberg, pp. 437-444, XP047461528, ISBN: 978-3-540-7 4549-5.
Koolwal Aditya B et al: "An Incremental Method for Registering Electroanatomic Mapping Data to Surface Mesh Models of the Left Atrium", Sep. 6, 2008 (Sep. 6, 2008), Advances in Biometrics : International Conference, ICB 2007, Seoul, Korea, Aug. 27-29, 2007 ; Proceedings; [Lecture Notes in Computer Science; Lect. Notes Computer], Springer, Berlin, Heidelberg, pp. 847-854, XP047462443, ISBN: 978-3-540-74549-5.
Summons to Attend Oral Proceedings dated Apr. 28, 2022 from related European Patent Application No. 19 188 855.1.
Antholzer, S. et al., "Deep Learning for Photoacoustic Tomography from Sparse Data", Inverse Problems in Science and Engineering, Aug. 18, 2017, vol. 27, No. 7, 20 pages.
Baram, A. et al., "Left Atria Reconstruction from a Series of Sparse Catheter Paths Using Neutral Networks", Intelligent Virtual Agent, IVA 2015, LNCS; [Lecture Notes in Computer Science; Lect. Notes Computer], Sep. 12, 2018, pp. 138-146.
Kurenkov, A. et al., "DeformNet: Free-Form Deformation Network for 3D Shape Reconstruction from a Single Image", Mar. 12, 2018, pp. 858-866.
European Search Report dated Nov. 5, 2019 in European Patent Application No. 19 18 8855.1.
Examination Report dated Nov. 26, 2020 from related EP 19 188.855.1.

* cited by examiner

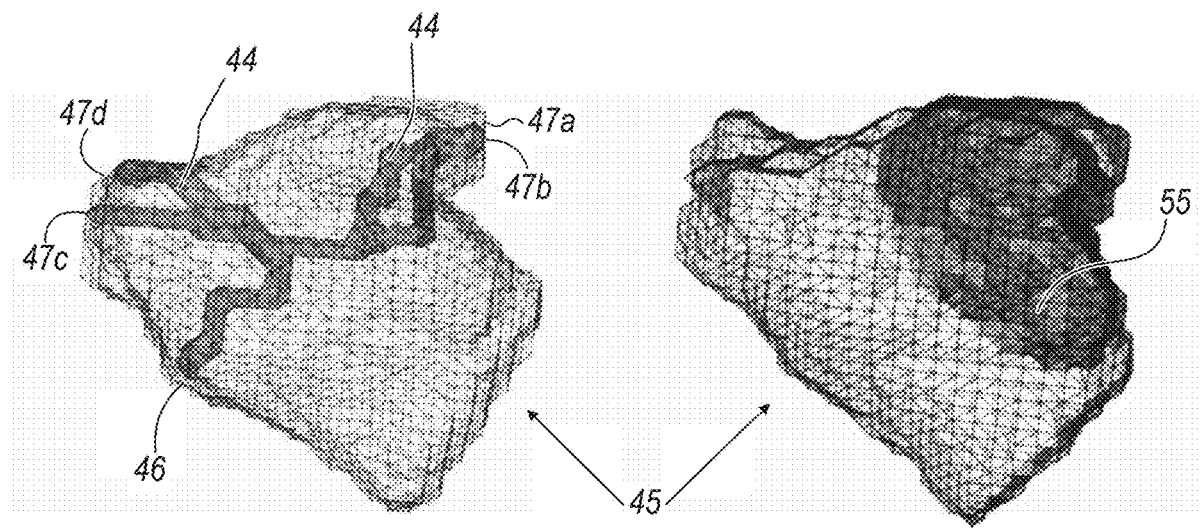
*FIG. 2A*   *FIG.2B*
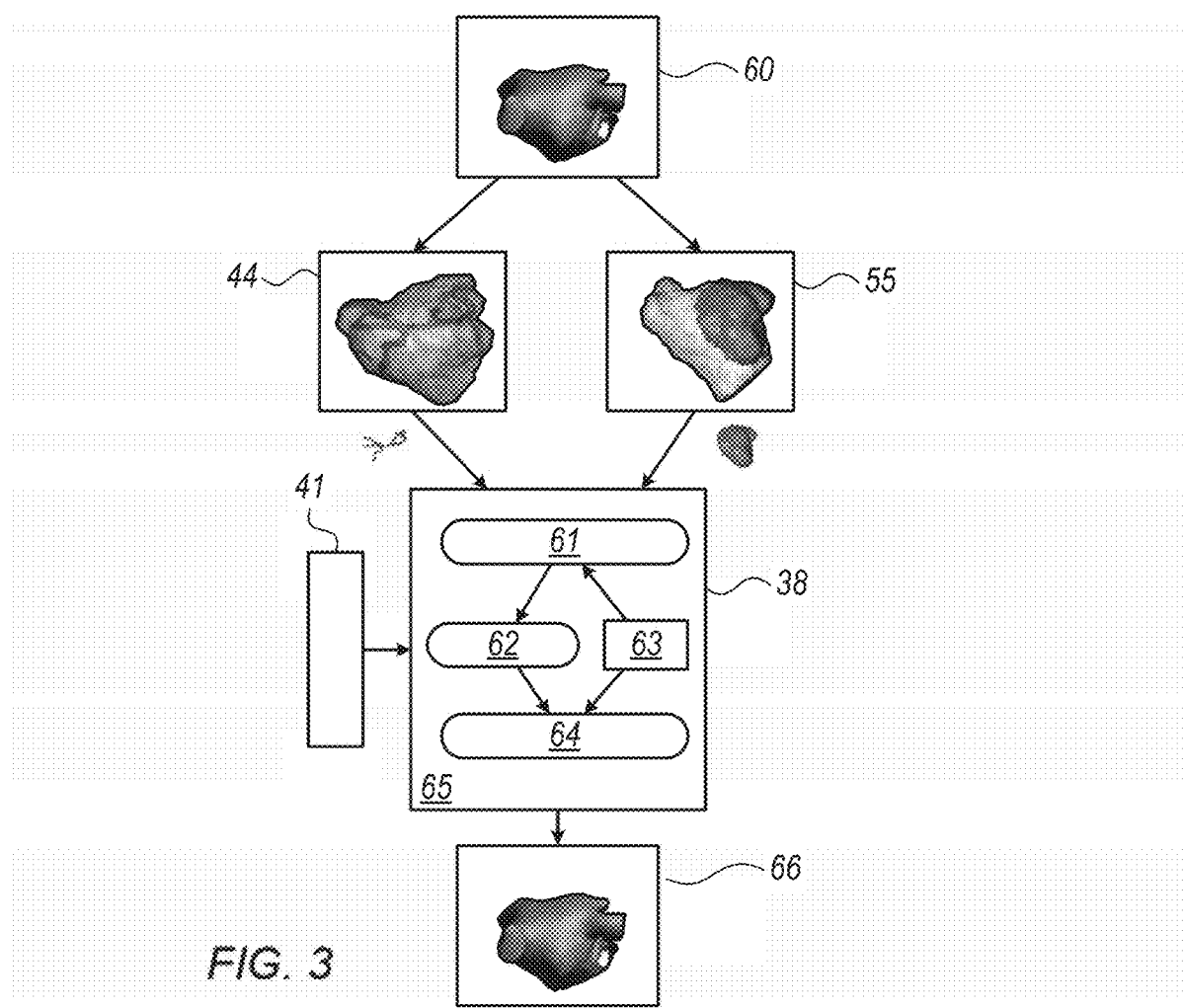
*FIG. 3*

LEFT ATRIUM SHAPE RECONSTRUCTION FROM SPARSE LOCATION MEASUREMENTS USING NEURAL NETWORKS

CROSS-REFERENCE TO RELATED APPLICATIONS

This application claims the benefit of U.S. Provisional Patent Application 62/711,814, filed Jul. 30, 2018, whose disclosure is incorporated herein by reference.

FIELD OF THE INVENTION

The present invention relates generally to cardiac mapping, and particularly to computation methods of anatomical cardiac maps.

BACKGROUND OF THE INVENTION

Some clinical procedures employ elaborated computation methods to generate an anatomical representation of an organ such as a cardiac chamber. For example, U.S. Patent Application Publication 2014/0152653 describes methods for processing two-dimensional ultrasound images from an intracardiac ultrasound imaging catheter, which provide improved image quality and enable generating three-dimensional composite images of the heart. Two-dimensional ultrasound images are obtained and stored in conjunction with correlating information, such as time or an electrocardiogram. Images related to particular conditions or configurations of the heart can be processed in combination to reduce image noise and increase resolution. Images may be processed to recognize structure edges, and the location of structure edges used to generate cartoon rendered images of the structure. Structure locations may be averaged over several images to remove noise, distortions and blurring from movement.

As another example, U.S. Patent Application Publication 2017/0046616 describes a use of 3D deep convolutional neural network architecture (DCNNA) equipped with so-called subnetwork modules which perform dimensionality reduction operations on 3D radiological volume before the 3D radiological volume is subjected to computationally expensive operations. Also, the subnetworks convolve 3D data at multiple scales by subjecting the 3D data to parallel processing by different 3D convolutional layer paths. Such multi-scale operations are computationally cheaper than the traditional CNNs that perform serial convolutions. In addition, performance of the subnetworks is further improved through 3D batch normalization (BN) that normalizes the 3D input fed to the subnetworks, which in turn increases learning rates of the 3D DCNNA. After several layers of 3D convolution and 3D sub-sampling with 3D across a series of subnetwork modules, a feature map with reduced vertical dimensionality is generated from the 3D radiological volume and fed into one or more fully connected layers.

SUMMARY OF THE INVENTION

An embodiment of the present invention provides a method, including, in a processor, receiving example representations of geometrical shapes of a given type of organ. In a training phase, a neural network model is trained using the example representations. In a modeling phase, the trained neural network model is applied to a set of location measurements acquired in an organ of the given type, to produce a three-dimensional model of the organ.

In some embodiments, the set of location measurements include location measurements over one or more paths of a catheter in the organ.

In some embodiments, the method includes training the neural network model to produce a smooth reconstruction.

In other embodiments, the method includes minimizing a regularization-function that comprises derivatives of weights of a first layer only of the neural-network model.

In an embodiment, the method includes receiving at least one example representation modality selected from the group of representation modalities consisting of a processed electro-anatomical map and processed medical images.

In another embodiment, the method includes applying the trained neural network model to locations measured by at least one measurement system selected from the group of measurement systems consisting of an electro-anatomical mapping system and a medical imaging modality.

In some embodiments, the organ is a left atrium of a heart.

There is additionally provided, in accordance with an embodiment of the present invention, a system, including a memory and a processor. The memory is configured to store example representations of geometrical shapes of a given type of organ. The processor is configured to (a) upload the example representations from the memory, (b) in a training phase, train a neural network model using the example representations, and store the trained neural network model in the memory, and (c) in a modeling phase, apply the trained neural network model to a set of location measurements acquired in an organ of the given type.

The present invention will be more fully understood from the following detailed description of the embodiments thereof, taken together with the drawings in which:

BRIEF DESCRIPTION OF THE DRAWINGS

FIGS. 2A and 2B are schematic, pictorial illustrations of regions over a left atrium where sets of locations were measured, in accordance with an embodiment of the present invention;

FIG. 3 is a block diagram that schematically illustrates a system for reconstructing a shape of a left atrium using a trained neural network model, in accordance with an embodiment of the present invention;

DETAILED DESCRIPTION OF EMBODIMENTS

Overview

Figure 1:
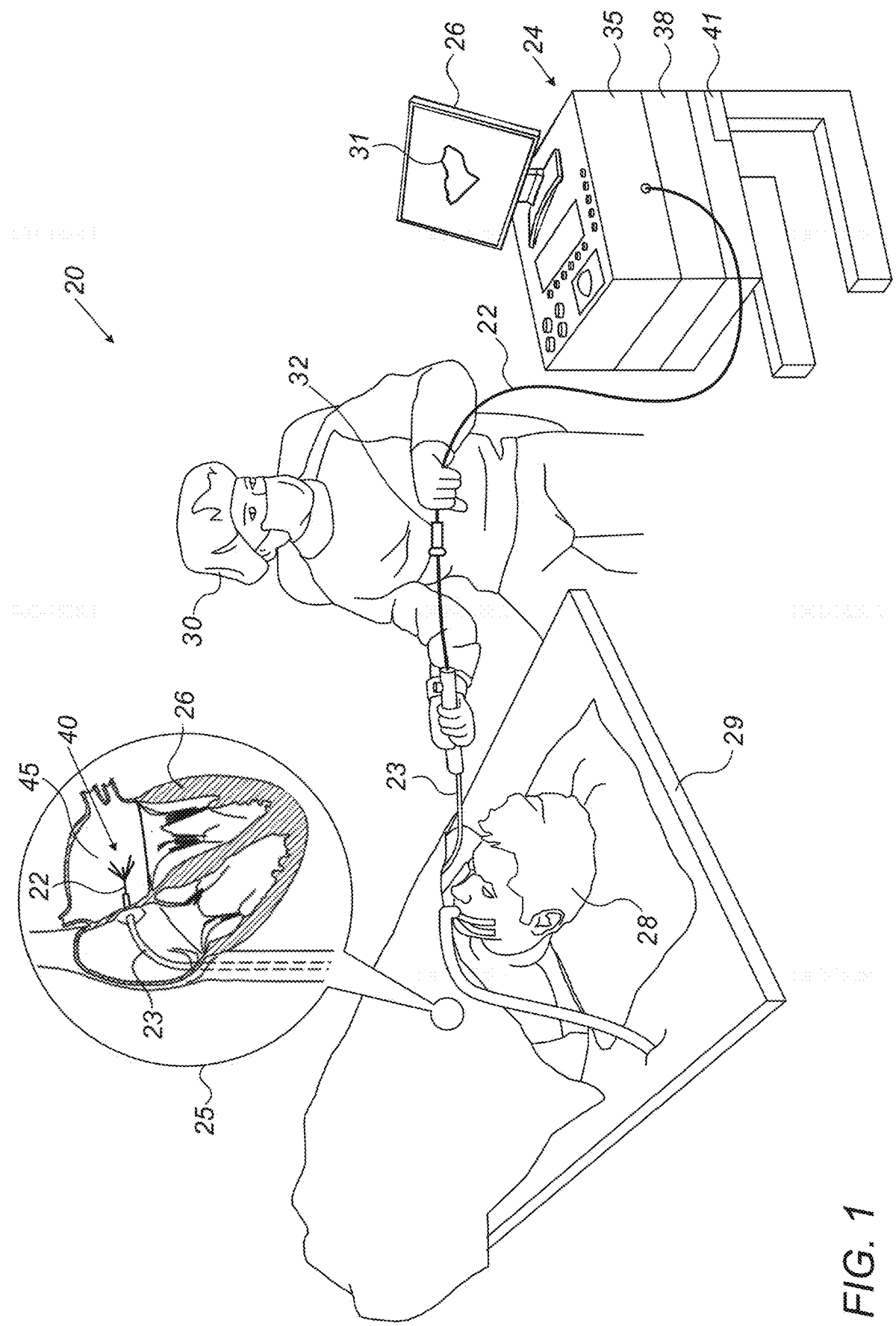
FIG. 1 is a schematic, pictorial illustration of a system for electro-anatomical mapping, in accordance with an embodiment of the present invention.

A cardiac chamber, such as a left atrium, has a geometrically complex shape that may be electro-anatomically mapped in a partial manner during a mapping procedure, such as using catheter-based anatomical mapping.

Methods for representing a left atrium from electro-anatomical data are provided, for example, in U.S. Pat. No. 9,576,107, which uses a physical model together with a statistical model, and whose disclosure is incorporated herein by reference. However, representations provided by existing methods tend to be noisy, and as noted above, only partial. In the present context, the term "partial" means that entire regions of the left atrium are not mapped. In such cases, naive interpolation or extrapolation of existing location measurements are practically useless.

Embodiments of the present invention that are described hereinafter utilize a database made of example representations of geometrical shapes of a given type of an organ, such as shapes of left atria of hearts of multiple different subjects, to (i) train a neural network model using the example representations, and (ii) in a modeling phase of a particular heart, apply the trained neural network model to a set of location measurements acquired in a left atrium of the particular heart in order to produce a three-dimensional model of that left atrium.

In some embodiments, the database of example representations of left atria shapes (i.e., representations of surfaces that represent each a boundary between blood pool and heart tissue are reconstructed from) is based on location measurements performed by a measurement system such an electro-anatomical mapping system and/or a medical imaging modality.

In some embodiments, the database of example representations of left atria shapes is constructed by processing medical imaging studies comprising a series of images, such as from Computerized Tomography (CT), Magnetic Resonance Imaging (MRI) and/or Ultrasound (US) modalities, using appropriate software. In an embodiment, the representations are extracted from medical images of portions of left atria using a sphere intersection model, as described below.

In some embodiments, in the modeling phase, a set of locations over a region of an inner surface of an organ, such as a region of the left atrium, is electro-anatomically measured. The acquisition occurs as a physician maneuvers a catheter, for example, from the trans-septal entry point to touch the major left and right pulmonary veins (PV) for initial anatomy orientation of the atrium. The catheter path performed by the physician may contain more information, as the physician usually slides the catheter across path boundaries to reach the PVs.

Based on the acquired locations, the disclosed trained neural network technique produces a three-dimensional model of the left atrium of the particular heart being investigated, i.e., completing the measured location data into a more complete representation of the left atrium, as described below.

The disclosed techniques reconstruct a realistic, and clinically valuable, shape of a cardiac chamber (e.g., a left atrium) from a sparse set of measured locations. By doing so, the disclosed technique and system may assist a physician in planning a proper treatment, such as a cardiac ablation. Since the disclosed techniques utilize only a sparse set of measurements, the mapping procedure may be shortened and simplified.

System Description

FIG. 1 is a schematic, pictorial illustration of a system 20 for electro-anatomical mapping, in accordance with an embodiment of the present invention. FIG. 1 depicts a physician 30 using an electro-anatomical catheter 40 to perform an electro-anatomical mapping of a cardiac chamber, such as a left atrium 45, of a heart 26 of a patient 28 laying on a table 29. By way of example, inset 25 shows catheter 40 as a PENTARAY® mapping catheter (made by Biosense-Webster, Irvine, Calif.), which comprises one or more arms which may be mechanically flexible, each of which being coupled with one or more mapping electrodes. As seen, catheter 40 is fitted at the distal end of a shaft 22.

During the mapping procedure, the mapping electrodes acquire and/or inject signals from and/or to the tissue of left atrium 45. A processor 38 in console 24 receives these signals via an electrical interface 35, and uses information contained in these signals to construct an electro-anatomical map 31. During and/or following the procedure, processor 38 may display electro-anatomical map 31 on a display 26. Typically, processor 38 stores electro-anatomical map 31 in memory 41.

Physician 30 navigates the distal end of a shaft 22 to a target location inside left atrium 45 of heart 26 by manipulating shaft 22 using a manipulator 32 near the proximal end of the catheter and/or deflection from the sheath 23. During the insertion of shaft 22, mapping catheter 40 is maintained in a collapsed configuration by sheath 23. By containing mapping catheter 40 in a collapsed configuration, sheath 23 also serves to minimize vascular trauma along the way to the target location.

During the procedure, a tracking system is used to track the respective locations of the mapping electrodes, such that each of the signals may be associated with the location at which the signal was acquired. For example, the Active Current Location (ACL) system, made by Biosense-Webster (Irvine, Calif.), which is described in U.S. Pat. No. 8,456,182, whose disclosure is incorporated herein by reference, may be used. In the ACL system, a processor estimates the respective locations of the electrodes based on impedances measured between each of the mapping-electrodes, and a plurality of surface-electrodes (not shown) that are coupled to the skin of patient 28. Processor 38 calculates a data-set of estimated locations along one or more paths of catheter 40 inside left atrium 45.

The example illustration shown in FIG. 1 is chosen purely for the sake of conceptual clarity. Other tracking methods can be used, such as ones based on measuring voltage signals, as with the Carto®4 system (produced by Biosense Webster). Other types of sensing catheters, such as the Lasso® Catheter (produced by Biosense Webster) may equivalently be employed. In an optional embodiment, processor 38 is further configured to indicate the quality of physical contact between each of the mapping electrodes and an inner surface of left atrium 45 during measurement.

Processor 38 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Left Atrium Shape Reconstruction from Sparse Catheter Measurements Using Neural Networks FIGS. 2A and 2B are schematic, pictorial illustrations of regions over a left atrium where sets of locations were measured, in accordance with an embodiment of the present invention. FIG. 2A shows an example path 44 along which mapping catheter 40 measured locations, for example, over an inner surface of left atrium 45. Path 44 begins at septum 46 which is the typical entry point of catheter 40 into left atrium 45. The path proceeds to the left superior PV 47a, left inferior PV 47b, right inferior PV 47c and finally to right superior PV 47d.

In additional or alternative embodiments, during a modeling phase, for example, the physician desires an improved representation of the left atrium obtained from electro-anatomical measurements over sparse catheter paths. To provide additional measured locations, a partial surface 55 (i.e., a region) of left atrium 45 is extracted from an imaged partial volume of left atrium 45, such as those acquired by a CT, US, or MRI imaging modality, as exemplified by FIG. 2B. In some embodiments, partial surface 55 is extracted from catheter measurements, such as measurements from multi-electrode catheters such as the PENTARAY® and/or LASSO® mapping catheters (made by Biosense-Webster), and/or use a balloon or a basket catheter.

To extract surface 55, the processor typically runs an image processing software, such as software that extracts a partial surface of left atrium 45 from medical images, using the sphere intersection model. In an embodiment, a random sphere is created with a center close enough to the center of the imaged atrium volume to have a reasonable intersection. The processor applies the software to place the selected sphere in intersection with the imaged left atria volume while requiring (e.g., by minimizing the loss function) the network model to reconstruct the full input, i.e., the complete representation of the left atrium.

The example illustrations shown in FIGS. 2A and 2B are chosen purely for the sake of conceptual clarity. FIGS. 2A and 2B only show parts relevant to embodiments of the present invention. Other details, such as the actual measured locations, are omitted for simplicity of presentation.

Based on the acquired locations, measured in either of the above described techniques, or others known, processor 38 uses the disclosed neural network computation technique to produce a three-dimensional model of left atrium 45, as described below.

In order to reconstruct a realistic volume of left atrium 45 from sparsely measured locations, the disclosed neural network computation technique uses a loss function (i.e., a neural network model), G, which includes a regularization-function, F, that comprises smoothing spatial weights, in addition to a cross-entropy loss term L. In some embodiments, L(x,z) is a logarithmic norm function, based on training, to achieve a "best fit" of z values to the measured locations x:

$$L(x, z) = \Sigma x \log(z) + (1-x)\log(1-z)$$

where x represents binary occupancy values (i.e., probabilities of being inside an atrium) for every coordinate in the volume of the measured locations, and z represents the binary occupancy values of the reconstructed volume. The summation (not shown explicitly) is performed over all coordinates of x, as described, for example, by Vincent et al., in "Extracting and Composing Robust Features with Denoising Autoencoders," Proceedings of the 25$^{th}$ ACM International Conference on Machine Learning, 2008, pages 1096-1103, which is incorporated herein by reference.

The complete neural network model function, G, is then given by:

$$G(x, z) = L(x, z) + F(x, z) = L(x, z) + \lambda \|\nabla_v W(x, z)\|^2$$

The above disclosed minimization of F(x,z) provides a smooth reconstruction, where the level of smoothing is set by a non-negative parameter λ. The function W(x,z) denotes a term comprising spatial weights, and an example of it is described in the above cited conference paper by P. Vincent et al. In the disclosed technique, W(x,z) is differentiated with respect to spatial dimensions v, forming a contractive autoencoder that penalizes non-smooth reconstructions.

In some embodiments of the present invention, the differentiation is performed on weights of an input layer (i.e., on weights of the first layer of the neural-network model). The above disclosed differentiation technique that is applied to the first layer is named hereinafter Weights Smoothing Regularization (WSR). In an embodiment, WSR results is sufficiently smooth 3D representation of a cardiac chamber, and thus, saves a need to include derivative of weights from additional layers in the regularization-function, F.

In an embodiment, the above functions are implemented discretely in software, so that, for example, a derivative with respect to v is computed using a finite difference method applied on matrix elements.

An example of an experimental application of the disclosed technique, using locations measured over a catheter path inside a left atrium laboratory phantom, and the application of G(x,z) to reconstruct the left atrium laboratory phantom, is provided in FIG. 5 below.

The neural network model is brought above by way of example. Other neural network models, e.g., ones that apply other metrics, such a different norm L, are possible, as would occur to a person skilled in the art.

FIG. 3 is a block diagram that schematically illustrates a system for reconstructing a shape of left atrium 45 using a trained neural network model, in accordance with an embodiment of the present invention.

Figure 5:
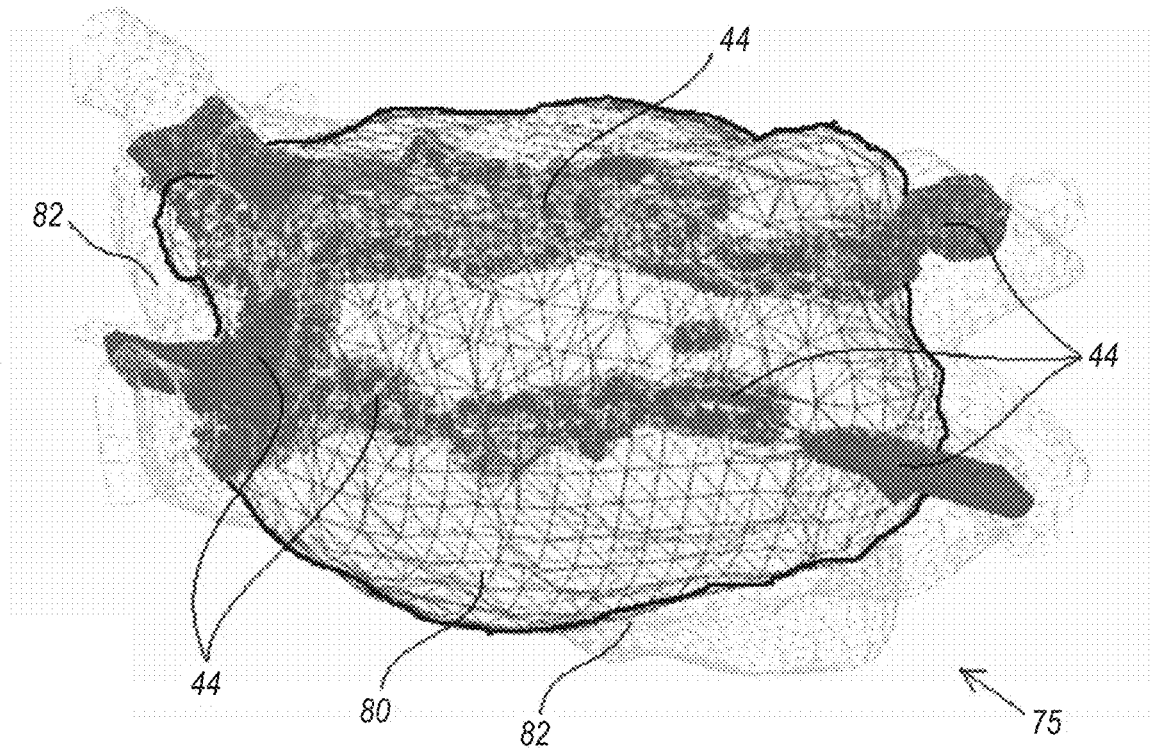
FIG. 5 is a schematic, pictorial illustration of a left atrium shape reconstruction of a laboratory phantom, in accordance with an embodiment of the present invention.

Object 60 is an actual left atrium, such as a laboratory phantom 75 of a left atrium of FIG. 5. The disclosed method is configured to reconstruct object 60 from an input layer 61 comprising sparse location measurements (e.g., paths 44 and/or partial surface 55 of FIGS. 2A and 2B, respectively). Input layer 61 and parameters of the trained neural network model are stored in memory 41.

To reconstruct object 60 from sparse data, processor applies an input layer 61 an autoencoder module 65 comprising a neural network module 62 and a regularization module 63. Processor 38 applies autoencoder 65 using a given number of hidden layers of the neural network model, and a given number of voxels to represent input layer 61. Processor 38 generates a 3D output layer 64 that is the reconstructed left atrium 66 (e.g., reconstructed left atrium 80 of FIG. 5) having a same given number of voxels as assigned to input layer 61, but one that comprises a learned left atrium shape that the sparse data best fit into.

Figure 4:
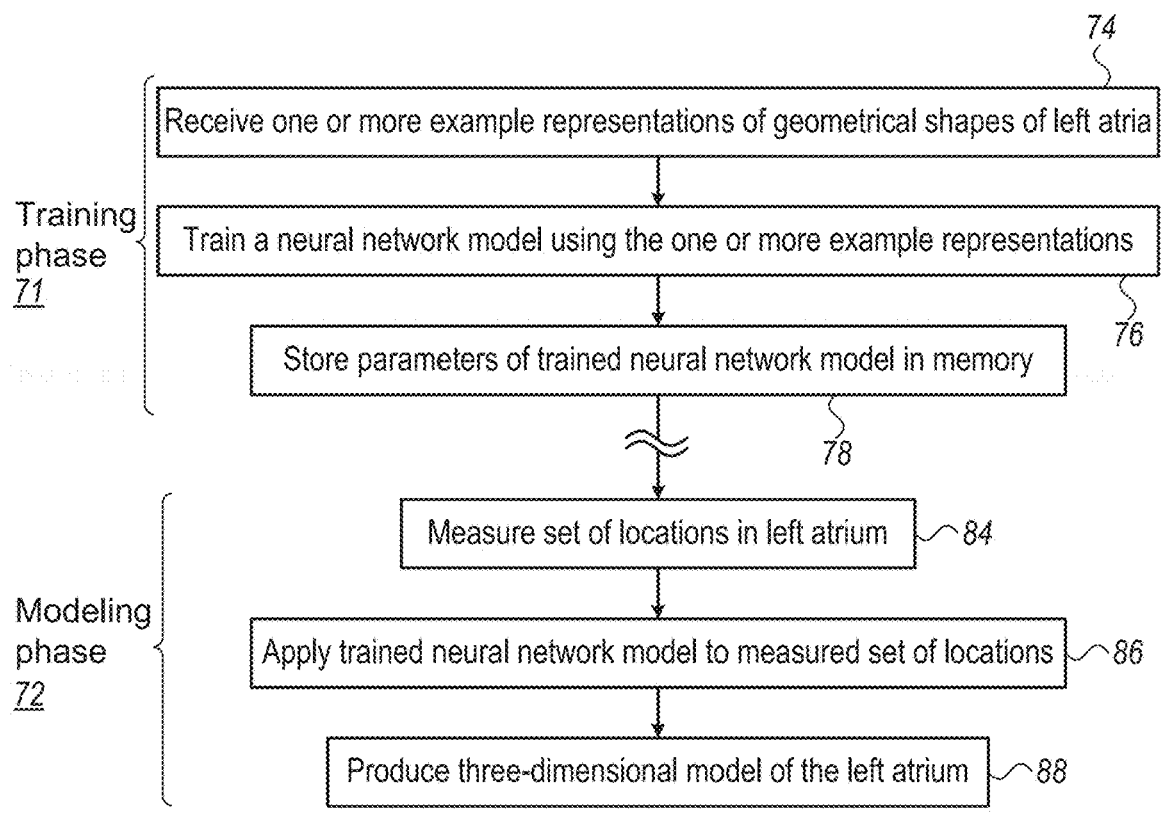
FIG. 4 is a flow-chart that schematically illustrates a method for reconstructing a shape of the left atrium using neural networks, in accordance with an embodiment of the present invention.

FIG. 4 is a flow-chart that schematically illustrates a method for reconstructing a shape of left atrium 45 using neural networks, in accordance with an embodiment of the present invention. The process begins with a training phase 71, after which the disclosed acquisition and modeling systems are operated in a modeling phase 72. The two phases may run at least partially in parallel while preforming a catheterization session.

Training phase 71 begins with processor 38 receiving example representations of geometrical shapes of left atria, at a database uploading step 74. Next, processor 38 runs the disclosed neural network model over the database of example representations, so as to train the network model, at a neural network training step 76. Finally, processor 38 stores the parameters of the trained neural network model in memory 41, or in a disk, or keep the model such way that the model can be directly loaded later during the procedure, at a storing step 78.

In modeling phase 72, electro-anatomical system 20 measures a set of locations in left atrium 45, as described above, in a locations acquisition step 84. Next, processor 38 runs the disclosed trained neural network model from step 76 over the measured set of locations, at a neural network model running step 86. Finally, processor 38 produces a three-dimensional model of left atrium 45, at a neural network modeling step 88.

The process may loop back to step 84 in order to receive more measured locations, for example from another region of heart 26, until the three-dimensional reconstruction is completed.

The example flow-chart shown in FIG. 4 is chosen purely for the sake of conceptual clarity. In alternative embodiments, additional steps may be performed, such as uploading medical images of left atrium 45 from memory 44 and extracting locations from the images, as described above, to provide additional locations for modeling step 86.

FIG. 5 is a schematic, pictorial illustration of a left atrium shape reconstruction 80 of a laboratory phantom 75, in accordance with an embodiment of the present invention. The reconstruction model applies neural networks to a database of locations obtained from sparse catheter path 44. A comparison is made against a ground truth 82, which is the actual shape of left atrium laboratory phantom 75. The set of locations along path 44 was acquired using an electro-anatomical tracking system 20, applied to laboratory phantom 75.

As seen, the acquired location over path 44, combined with a neural network shape reconstruction 80, yields a three-dimensional model of the left-atrium phantom that is substantially complete, and adequately agrees, with the actual shape of left atrium laboratory phantom 75. Thus, reconstructed shape 80, together with acquired locations over path 44, allows a physician to draw, for example, contours over shape 80 which indicate where to ablate a real (e.g., ground truth 82 in the described case) left atrium tissue to suppress an arrhythmia.

The illustration shown in FIG. 5 is brought purely by way of example, for the sake of conceptual clarity. Any actual shape, for example, may be reconstructed by the disclosed technique using additional information on top of that based on electro-anatomical catheter 40 paths, such as on medical images of left atrium 45.

Although the embodiments described herein mainly address cardiac applications, the methods and systems described herein can also be used in other medical applications, such as for producing three-dimensional models of other organs based on sparse data.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   in a processor, receiving example representations of geometrical shapes of a given type of organ;
   in a training phase, training a neural network model using the example representations to produce a smooth reconstruction, wherein the neural network model comprises a regularization function comprising smoothing spatial weights; and
   in a modeling phase, applying the trained neural network model to a set of location measurements acquired in an organ of the given type, to produce a three-dimensional model of the organ.

2. The method according to claim 1, wherein the set of location measurements comprises location measurements over one or more paths of a catheter in the organ.

3. The method according to claim 1, wherein producing the smooth reconstruction comprises minimizing the regularization-function that comprises derivatives of the spatial weights of a first layer only of the neural-network model.

4. The method according to claim 1, wherein receiving the example representations comprises receiving at least one example representation modality selected from the group of representation modalities consisting of a processed electro-anatomical map and processed medical images.

5. The method according to claim 1, wherein applying the trained neural network model comprises applying the trained neural network model to locations measured by at least one measurement system selected from the group of measurement systems consisting of an electro-anatomical mapping system and a medical imaging modality.

6. The method according to claim 1, wherein the organ is a left atrium of a heart.

7. A system, comprising:
   a memory, which is configured to store example representations of geometrical shapes of a given type of organ; and
   a processor, which is configured to:
      upload the example representations from the memory;
      in a training phase, train a neural network model using the example representations to produce a smooth reconstruction, wherein the neural network model comprises a regularization function comprising smoothing spatial weights, and store the trained neural network model in the memory; and
      in a modeling phase, apply the trained neural network model to a set of location measurements acquired in an organ of the given type.

8. The system according to claim 7, wherein the set of location measurements comprises location measurements over one or more paths of a catheter in the organ.

9. The system according to claim 7, wherein the processor is configured to produce the smooth reconstruction by minimizing the regularization-function that comprises derivatives of the spatial weights of a first layer only of the neural-network model.

10. The system according to claim 7, wherein the processor is configured to receive at least one example representation modality, selected from the group of representation modalities consisting of a processed electro-anatomical map and processed medical images.

11. The system according to claim 7, wherein the processor is configured to apply the neural network model to location measurements obtained by at least one measurement system selected from the group of measurement systems consisting of an electro-anatomical mapping system and a medical imaging modality.

12. The system according to claim 7, wherein the organ is a left atrium of a heart.

13. A method, comprising:
in a processor, receiving example representations of geometrical shapes of a given type of organ;
in a training phase, training a neural network model using the example representations to produce a smooth reconstruction by minimizing a regularization-function that comprises derivatives of weights of a first layer only of the neural-network model; and
in a modeling phase, applying the trained neural network model to a set of location measurements acquired in an organ of the given type, to produce a three-dimensional model of the organ.

14. The method according to claim 13, wherein the set of location measurements comprises location measurements over one or more paths of a catheter in the organ.

15. The method according to claim 13, wherein applying the trained neural network model comprises applying the trained neural network model to locations measured by at least one measurement system selected from the group of measurement systems consisting of an electro-anatomical mapping system and a medical imaging modality.

16. A system, comprising:
a memory, which is configured to store example representations of geometrical shapes of a given type of organ; and
a processor, which is configured to:
upload the example representations from the memory;
in a training phase, train a neural network model using the example representations to produce a smooth reconstruction by minimizing a regularization-function that comprises derivatives of weights of a first layer only of the neural-network model; and
in a modeling phase, applying the trained neural network model to a set of location measurements acquired in an organ of the given type, to produce a three-dimensional model of the organ.

17. The system according to claim 16, wherein the set of location measurements comprises location measurements over one or more paths of a catheter in the organ.

18. The system according to claim 16, wherein the processor is configured to apply the neural network model to location measurements obtained by at least one measurement system selected from the group of measurement systems consisting of an electro- anatomical mapping system and a medical imaging modality.

* * * * *